United States Patent
Lu

(10) Patent No.: US 10,154,985 B2
(45) Date of Patent: *Dec. 18, 2018

(54) METHOD FOR TREATING A GLYCOPROTEIN-RELATED DISEASE

(71) Applicant: Ming-Chang Lu, New Taipei (TW)

(72) Inventor: Ming-Chang Lu, New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,512

(22) Filed: Aug. 15, 2016

(65) Prior Publication Data

US 2017/0049742 A1  Feb. 23, 2017

(30) Foreign Application Priority Data

Aug. 19, 2015  (TW) .............................. 104127036 A
Feb. 27, 2016  (TW) .............................. 105106052 A

(51) Int. Cl.
| | | |
|---|---|---|
| *A61K 31/285* | (2006.01) | |
| *A61K 31/185* | (2006.01) | |
| *A61K 31/10* | (2006.01) | |
| *A61K 45/06* | (2006.01) | |

(52) U.S. Cl.
CPC ............ *A61K 31/285* (2013.01); *A61K 31/10* (2013.01); *A61K 31/185* (2013.01); *A61K 45/06* (2013.01)

(58) Field of Classification Search
None
See application file for complete search history.

(56) References Cited

U.S. PATENT DOCUMENTS

2004/0001896 A1*  1/2004  Kuppam .............. A61K 36/185
424/734

FOREIGN PATENT DOCUMENTS

| CN | 103751210 A | 4/2014 |
| TW | 201607532 A | 3/2016 |
| WO | 03032969 A | 4/2003 |

OTHER PUBLICATIONS

ISMRD, About glycoprotein diseases, http://www.ismrd.org/glycoprotein_diseases, Dec. 31, 2014.*
Kegelangzhen, TA Foong Chemicial & Pharmaceutical Co., Ltd., Oct. 1, 1986, 2 pages.
R.Latha, R.Nagashree, V.Karthikeyan and C. Anand, Effect of Phenol Red on Blood Cell Counts of Arsenate Exposed Albino Mice, Biomedicine 2007; 27 (2): 60-63.
R. Latha, Rashmi P. Rao and J. Prakasa RAO3, Phenol Red Inhibits Arsenate Uptake by the Everted Gut Sacs of Mice and Reduces Its Toxicity, Pharmacologyonline 3: 677-696 (2010).

* cited by examiner

*Primary Examiner* — Celeste A Roney

(57) ABSTRACT

A method for treating a glycoprotein-related disease is disclosed, which comprises: administering a first effective amount of phenol red and a second effective amount of an organic arsenic compound to a subject in need thereof.

11 Claims, 1 Drawing Sheet

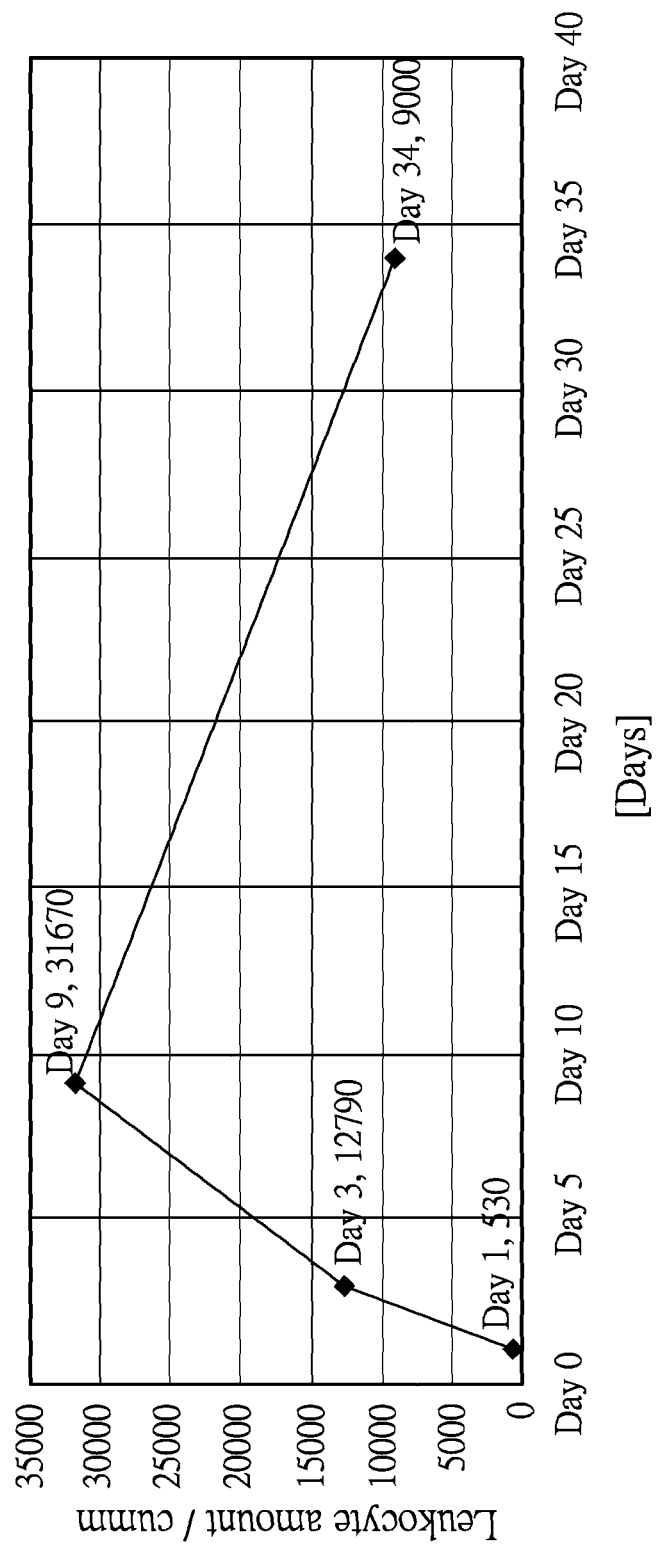

METHOD FOR TREATING A GLYCOPROTEIN-RELATED DISEASE

CROSS REFERENCE TO RELATED APPLICATION

This application claims the benefits of the Taiwan Patent Application Serial Number 104127036, filed on Aug. 19, 2015, the subject matter of which is incorporated herein by reference.

This application also claims the benefits of the Taiwan Patent Application Serial Number 105106052, filed on Feb. 27, 2016, the subject matter of which is incorporated herein by reference.

BACKGROUND

1. Field of the Invention

The present invention relates to a pharmaceutical composition and a method for treating a glycoprotein-related disease and, more particularly, to a pharmaceutical composition and a method for treating a glycoprotein-related disease with phenol red and an organic arsenic compound.

2. Description of Related Art

Currently, clinical treatment of viral diseases is mainly based on supportive therapy. Supportive therapy involves fluid therapy and nutrition supplementation to help patients recuperate and to increase immunity. It also involves concurrent administration of broad-spectrum antibiotics to prevent secondary infection. However, whether viral diseases can be cured depends on individual's immunity.

Treatment of snake venom infection requires an initial determination of the infection to be hemorrhagic venom infection or neurotoxic venom infection. Administration of anti-snake venom serum then follows to neutralize toxicity and to increase immunity. With concurrent administration of antibiotics, healing time of wounds with redness and swelling is over 7 days.

Prion infection, such as bovine spongiform encephalopathy, scrapie, and Creutzfeldt-Jakob disease, is caused by abnormal cellular metabolism due to glycosylation between carbohydrates and proteins in brain cells. Such abnormal cellular metabolism results in denaturation of proteins to infective proteins as well as deposition and aggregation of glycoproteins and amyloids to induce neuropathy. Until now, there is still no effective drug treatment and prevention for Prion infection.

Toxic protein infection by insects and reptiles, such as mosquitoes, bees, scorpions, spiders, centipedes, ants, and staphylinidae, is caused by injection of toxic proteins into mankind and animals by stinging. The result ranges from redness, swelling, allergy, itching, and inflammation of skin to fever. Such insects and reptiles also play roles as media or carriers of viruses, such as dengue viruses that belong to Flaviviridae and Flavivirus, West Nile virus, and Zika virus, to infect mankind and animals.

Cell abnormality includes pathological changes of eye cells, brain cells, and cellular metabolism. Cataract, one of the pathological changes of eye cells, is caused by abnormal metabolism and degeneration in the elderly. Such abnormal metabolism and degeneration result in abnormal glycosylation between carbohydrates and proteins in cells of eye lens. Cataract membrane formation due to deposition and aggregation of protein fibers leads to blurred vision. The current treatment of cataract includes surgical removal and laser treatment. However, such treatments are not completely pain-free and have risks for blindness as well as high surgery cost. Retinopathy, another pathological change of eye cells, is caused by glycosylation between carbohydrates and proteins in photoreceptors cells of fiber membrane and choroidal membrane of retina. Such glycosylation leads to degeneration and vision loss. The treatment of retinopathy generally includes supplementation of vitamin A and lutein. However, such treatment has no active therapeutic effect.

Alzheimer's disease, one of the pathological changes of brain cells, is also caused by glycosylation between carbohydrates and proteins in brain cells. Such glycosylation results in abnormal cellular metabolism as well as deposition and aggregation of glycoproteins and amyloids. These induce symptoms of dementia, memory loss, and degeneration of the elderly. Currently, there is no effective prevention and treatment of Alzheimer's disease. Parkinson's disease is also caused by glycosylation between carbohydrates and proteins in neurons of brain. Such glycosylation results in abnormal metabolism, neurodegeneration, as well as deposition and aggregation of amyloids and fibrins, leading to chronic neurological symptoms. There is also no prevention and effective treatment of Parkinson's disease.

Pancreatitis, a pathological change of cellular metabolism, is caused by glycosylation between carbohydrates and proteins in pancreatic cells. Such glycosylation results in abnormal cellular metabolism, degeneration, as well as deposition and aggregation of glycoproteins and amyloids. These lead to swelling of pancreas, acute and chronic inflammation, and fibrosis of pancreas. Such pancreatitis is often categorized as having unknown causes medically. Treatment of such pancreatitis depends on autologous immunity. There is no effective drug treatment for such pancreatitis. Kidney inflammation is caused by glycosylation between carbohydrates and proteins in renal cells. Such glycosylation results in abnormal cellular metabolism and degeneration as well as deposition and aggregation of amyloids. These lead to swelling of kidney, acute and chronic inflammation, and fibrosis of kidney. Such kidney inflammation is often categorized as having unknown causes medically. There is no effective drug treatment for such kidney inflammation. Hepatitis and cholangitis are caused by glycosylation between carbohydrates and proteins in hepatic cells. Such glycosylation results in abnormal cellular metabolism as well as deposition and aggregation of glycoproteins and amyloids. These lead to swelling and inflammation of liver and bile duct as well as fibrosis of liver. Medically, such hepatitis and cholangitis are categorized as acute fulminating hepatitis, acute hepatitis, acute cholangitis, or having other unknown causes. There is no effective drug treatment for such hepatitis and cholangitis.

Accordingly, there is a need to develop an effective drug for treating the aforesaid diseases.

SUMMARY

The present disclosure provides a method for treating a glycoprotein-related disease, which comprises: administering a first effective amount of phenol red and a second effective amount of an organic arsenic compound to a subject in need thereof.

The present disclosure also provides a pharmaceutical composition for treating a glycoprotein-related disease in a subject in need thereof, which comprises: a first effective amount of phenol red and a second effective amount of an organic arsenic compound.

Furthermore, the present disclosure provides a use of a pharmaceutical composition for manufacturing a medicine for treating a glycoprotein-related disease, wherein the pharmaceutical composition comprises: a first effective amount of phenol red and a second effective amount of an organic arsenic compound.

Phenol red is known as an acid-base indicator and a diagnosis medicine. The arsenic compound is known as a medicine for treating syphilis, a blood agent, an herbicide and an insecticide.

In the present disclosure, the phenol red and the organic arsenic compound are co-used to inhibit the interaction between carbohydrates and proteins and the glycosylation on proteins in pathogens.

When the phenol red and the organic arsenic compound are co-used, the glycosylation pathway between the carbohydrates (such as sugar, starch and cellulose) and proteins, nucleoside and enzyme of pathogens (such as snake venom, prion, insect venom, reptile venom, virus and abnormal cells) can be inhibited; and the diseases and disorders caused by the pathogens can be inhibited. Hence, the combination of the phenol red and the organic arsenic compound can be used to treat or prevent virus infection (including DN and RNA viruses with different structures and shapes), snake venom infection (including hemorrhagic venom infection and neurotoxic venom infection), prion infection (including bovine spongiform encephalopathy, scrapie, and creutzfeldt-Jakob disease), insect venom infection (including mosquito's infection, bee's venom infection, scorpion's venom infection, spider's venom infection, centipede's venom infection, ant's venom infection, and staphylinidae's venom infection), reptile venom infection, a disease caused by abnormal eye cells (including cataract and retinopathy), a disease caused by abnormal brain cells (including Alzheimer's Disease and Parkinson's disease), and cell metabolism-related diseases (including pancreatitis, kidney inflammation, hepatitis, and cholangitis) occurred in vertebrate (preferably, mammalian).

In the present disclosure, when the pharmaceutical composition of the phenol red and the organic arsenic compound are used, the treating efficacy of the combination is better than that of the organic arsenic compound alone, and the application field of the pharmaceutical composition is also larger than that of the organic arsenic compound alone. In addition, in the present disclosure, the experimental results indicate the pharmaceutical composition of the present disclosure has good treating effect on various diseases caused by different pathogens. The reason is that the active ingredients can combine with the receptors of the glycoproteins in the pathogens, enter into the proteomic of the pathogens, and then restrict the localizations of the protein particles. Next, the morphology of the protein particles is changed, and the activity thereof is loss. Hence, the pathogens cannot perform their metabolism and synthesis in the host cells, the polymerization of amino acids for forming proteins is inhibited, and then the glycosylation of the pathogens is further inhibited, resulting in the structure of the protein changed, the apoptosis of the proteins, and the synthesis, replication and differentiation of the pathogens inhibited. Therefore, the glycosylation pathway between the carbohydrates (such as sugar, starch and cellulose) and proteins, nucleoside and enzyme of the pathogens can be inhibited, and the diseases and disorders caused by the pathogens can be inhibited when the pharmaceutical composition of the present disclosure is used.

In addition, the phenol red in the pharmaceutical composition of the present disclosure can be used as a stabilizer of the organic arsenic compound (such as monosodium methanearsonate).

In the present disclosure, the phenol red and the organic arsenic compound can be combined into one formulation, or used in two separated formulations.

In the present disclosure, the organic arsenic compound can be selected from the group consisting of monosodium methanearsonate, methylarsonic acid, sodium dimethylarsonate, disodium methylarsonate, cacodylic acid, and calcium acid methanearsonate.

In the present disclosure, the phenol red has molecular weight of 354, and CAS No. thereof is 143-74-8. Monosodium methanearsonate has molecular weight of 162, and CAS No. thereof is 2163-80-6.

In the present disclosure, the glycoprotein-related disease can be caused by various viruses. Herein, the viruses classified by National Center for Biotechnology Information, U.S. are listed below.

Family: Retroviridae
- Subfamily: Orthoretrovirinae
- Genus: *Alpharetrovirus*
  - species: *Avian leukosis* virus
- Genus: *Betaretrovirus*
  - species: *Jaagsiekte sheep retrovirus*
- Genus: *Deltaretrovirus*
  - species: *Bovine leukemia* virus
  - species: *Primate T-lymphotropic* virus 1
  - species: *Primate T-lymphotropic* virus 2
  - species: *Primate T-lymphotropic* virus 3
- Genus: *Gammaretrovirus*
  - species: *Feline leukemia* virus
  - species: *Gibbon ape leukemia* virus (GALV)
  - species: *Porcine type-C oncovirus*
- Genus: *Lentivirus*
  - species: *Bovine immunodeficiency* virus
  - species: *Equine infectious anemia* virus
  - species: *Feline immunodeficiency* virus
  - species: *Human immunodeficiency* virus 1
  - species: *Human immunodeficiency* virus 2
  - species: *Puma lentivirus*
  - species: *Simian immunodeficiency* virus
  - species: *Visna/maedi* virus
- Subfamily: Spumaretrovirinae
- Genus: *Spumavirus*
  - species: *African green monkey simian foamy* virus
  - species: *Bovine foamy* virus
  - species: *Equine foamy* virus
  - species: *Feline foamy* virus
  - species: *Macaque simian foamy* virus
  - species: *Simian foamy* virus Family: Parvoviridae
- Subfamily: Parvovirinae
- Genus: *Aveparvovirus*
  - species: *Chicken parvovirus*
  - species: *Chicken parvovirus* ABU-P1
  - species: *Gallus gallus enteric parvovirus*
  - species: *Turkey parvovirus* 260
- Genus: *Bocaparvovirus*
  - species: *Pinniped bocaparvovirus* 1
  - species: *Pinniped bocaparvovirus* 2
  - species: *Primate bocaparvovirus* 1
  - species: *Primate bocaparvovirus* 2
  - species: *Ungulate bocaparvovirus* 1
  - species: *Ungulate bocaparvovirus* 2
  - species: *Ungulate bocaparvovirus* 3
  - species: *Ungulate bocaparvovirus* 4
  - species: *Ungulate bocaparvovirus* 5

Genus: *Copiparvovirus*
  species: *Ungulate copiparvovirus* 1
  species: *Ungulate copiparvovirus* 2
Genus: *Erythroparvovirus*
  species: *Primate erythroparvovirus* 1
  species: *Primate erythroparvovirus* 2
  species: *Primate erythroparvovirus* 3
  species: *Primate erythroparvovirus* 4
  species: *Ungulate erythroparvovirus* 1
Genus: *Protoparvovirus*
  species: *Canine parvovirus*
  species: *Feline panleukopenia* virus (strain 193)
  species: *Porcine parvovirus*
Genus: *Tetraparvovirus*
  species: *Primate tetraparvovirus* 1
  species: *Ungulate tetraparvovirus* 1
  species: *Ungulate tetraparvovirus* 2
  species: *Ungulate tetraparvovirus* 3
  species: *Ungulate tetraparvovirus* 4
Family: Paramyxoviridae
  Subfamily: Paramyxovirinae
    Genus: *Avulavirus*
      species: *Avian paramyxovirus* 2
      species: *Avian paramyxovirus* 3
      species: *Avian paramyxovirus* 4
      species: *Avian paramyxovirus* 5
      species: *Avian paramyxovirus* 6
      species: *Avian paramyxovirus* 7
      species: *Avian paramyxovirus* 8
      species: *Avian paramyxovirus* 9
      species: *Avian paramyxovirus* 10
      species: *Avian paramyxovirus* 11
      species: *Avian paramyxovirus* 12
      species: *Newcastle disease* virus
    Genus: *Henipavirus*
      species: *Hendra* virus
      species: *Nipah* virus
    Genus: *Morbillivirus*
      species: *Canine distemper* virus
      species: *Measles* virus
      species: *Rinderpest* virus
    Genus: *Respirovirus*
      species: *Bovine parainfluenza* virus 3
      species: *Human parainfluenza* virus 1
      species: *Human parainfluenza* virus 3
      species: *Porcine parainfluenza* virus 1
      species: *Sendai* virus
    Genus: *Rubulavirus*
      species: *Human parainfluenza* virus 2
      species: *Human parainfluenza* virus 4
      species: *Mapuera* virus
      species: *Mumps* virus
      species: *Parainfluenza* virus 5
      species: *Porcine rubulavirus*
      species: *Simian* virus 41
  Subfamily: Pneumovirinae
    Genus: *Metapneumovirus*
      species: *Avian metapneumovirus*
      species: *Human metapneumovirus*
    Genus: *Orthopneumovirus*
      species: *Bovine respiratory syncytial* virus
      species: *Human respiratory syncytial* virus
      species: *Murine pneumonia* virus
    Genus: *Pneumovirus*
      species: *Canine pneumovirus*
      species: *Feline pneumovirus*
      species: *Human respiratory syncytial* virus A
      species: *Human respiratory syncytial* virus B
      species: *Human respiratory syncytial* virus S2
      species: *Human respiratory syncytial* virus strain RSS-2
      species: *Human respiratory syncytial* virus MinA
      species: *Human respiratory syncytial* virus MinB
      species: *Human respiratory syncytial* virus MinFLC
      species: *Human respiratory syncytial* virus MinL
      species: *Ovine respiratory syncytial* virus
      species: *Pneumovirus* dog/Ane4/USA/2008
      species: *Pneumovirus* dog/Bme17/USA/2008
      species: *Pneumovirus* HFR-2013
      species: *Respiratory syncytial* virus type A
Family: Coronaviridae
  Subfamily: Coronavirinae
    Genus: *Alphacoronavirus*
      species: *Canine coronavirus*
      species: *Feline coronavirus*
      species: *Human coronavirus* 229E
      species: *Human coronavirus* NL63
      species: *Porcine epidemic diarrhea* virus
      species: *Transmissible gastroenteritis* virus
    Genus: *Betacoronavirus*
      species: *Bovine coronavirus*
      species: *Canine respiratory coronavirus*
      species: *Equine coronavirus*
      species: *Human coronavirus* OC43
      species: *Porcine hemagglutinating encephalomyelitis* virus
      species: *Human coronavirus* HKU1
      species: *Human coronavirus* type 5
      species: *Middle East respiratory syndrome coronavirus*
      species: *Severe acute respiratory syndrome-related coronavirus*
    Genus: *Deltacoronavirus*
      species: *Porcine coronavirus* HKU15
    Genus: *Gammacoronavirus*
      species: *Duck coronavirus*
      species: *European turkey coronavirus* 080385d
      species: *Goose coronavirus*
      species: *Infectious bronchitis* virus
      species: *Pheasant coronavirus*
      species: *Pigeon coronavirus*
      species: *Turkey coronavirus*
  Subfamily: Torovirinae
    Genus: *Torovirus*
      species: *Bovine torovirus*
      species: *Equine torovirus*
      species: *Human torovirus*
      species: *Porcine torovirus*
Family: Herpesviridae
  Subfamily: Alphaherpesvirinae
    Genus: *Iltoviru*
      species: *Gallid herpesvirus* 1
      species: *Psittacid herpesvirus* 1
    Genus: *Mardivirus*
      species: *Anatid herpesvirus* 1
      species: *Columbid herpesvirus* 1
      species: *Gallid herpesvirus* 2
      species: *Gallid herpesvirus* 3
      species: *Meleagrid herpesvirus* 1 (*Turkey herpesvirus*)
    Genus: *Simplexvirus*
      species: *Bovine herpesvirus* 2
      species: *Human herpesvirus* 1 (*Herpes simplex* virus type 1)
      species: *Human herpesvirus* 2
      species: *Macacine herpesvirus* 1 (monkey B virus)

Genus: *Varicellovirus*
  species: *Bovine herpesvirus* 1
  species: *Bovine herpesvirus* 5
  species: *Canid herpesvirus* 1
  species: *Caprine herpesvirus* 1 (*goat herpesvirus*)
  species: *Equid herpesvirus* 1 (*Equine herpesvirus* 1)
  species: *Equid herpesvirus* 3
  species: *Equid herpesvirus* 4 (*Equine herpesvirus* 4)
  species: *Equid herpesvirus* 8
  species: *Equid herpesvirus* 9
  species: *Felid herpesvirus* 1
  species: *Human herpesvirus* 3 (*Varicella-zoster* virus)
  species: *Suid herpesvirus* 1 (*Pseudorabies* virus)
Subfamily: Betaherpesvirinae
Genus: *Cytomegalovirus*
  species: *Aotine herpesvirus* 1
  species: *Cebine herpesvirus* 1
  species: *Human herpesvirus* 5 (*Human cytomegalovirus*)
  species: *Macacine herpesvirus* 3 (*Rhesus cytomegalovirus*)
  species: *Panine herpesvirus* 2 (*Chimpanzee cytomegalovirus*)
Genus: *Proboscivirus*
  species: *Elephantid herpesvirus* 1
Genus: *Roseolovirus*
  species: *Human herpesvirus* 6A
  species: *Human herpesvirus* 6B
  species: *Human herpesvirus* 7
Subfamily: Gammaherpesvirinae
Genus: *Lymphocryptovirus*
  species: *Human herpesvirus* 4 (*Epstein-Barr* virus)
Genus: *Macavirus*
  species: *Bovine herpesvirus* 6
  species: *Caprine herpesvirus* 2
  species: *Ovine herpesvirus* 2
Genus: *Percavirus*
  species: *Equid herpesvirus* 2 (*Equine herpesvirus* 2)
  species: *Equid herpesvirus* 5
Genus: *Rhadinovirus*
  species: *Bovine herpesvirus* 4
  species: *Human herpesvirus* 8

In the present disclosure, a pharmaceutical acceptable carrier can be further administered to the subject in need thereof. Hence, the pharmaceutical composition of the present disclosure may further comprises the pharmaceutical acceptable carrier. Herein, the pharmaceutical acceptable carrier is selected from the group consisting of solvent, buffer (such as phosphate buffered saline (PBS), Ringer's solution and Hank's solution), suspending agent, decomposer, disintegrating agent, dispersing agent, binding agent, excipient, stabilizing agent, chelating agent, diluent, gelling agent, preservative, lubricant, absorption delaying agent, and liposome.

In the present disclosure, the pharmaceutical composition can be formulated into any formulation known in the art. The formulations comprise, but are not limited to: injection (for example, sterile aqueous solution or dispersion), sterile powder, tablet, troche, patch, lozenge, capsule, dispersible powder or granule, solution, suspension, emulsion, syrup, elixir, slurry and the like.

In the present disclosure, the term "treating" or refers to administering the phenol red and the organic arsenic compound to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

In the present disclosure, the term "a first or second effective amount" refers to the amount of the phenol red or the organic arsenic compound that is required to confer a therapeutic effect on the treated subject. Effective amounts may vary, as recognized by those skilled in the art, depending on the types of diseases treated, route of administration, excipient usage, and the possibility of co-usage with other agents.

In the present disclosure, the phenol red and the organic arsenic compound can be administered via any known rout known in the art, for example, parenteral routes, intraperitoneal injection, subcutaneous injection, intramuscular injection and intravenous injection. Preferably, the phenol red and the organic arsenic compound are administered via intramuscular injection or intravenous injection.

In the present disclosure, the dose and the administering times of the phenol red and the organic arsenic compound can be varied based on the following factors: the severity of the disease to be treated, the administering rout, and the age, condition and reaction of the subject to be treated. Generally, the dose of the phenol red and the organic arsenic compound is administered based on the bodyweight of the subject, and can be administered in a single dosage or several dosages, as long as the phenol red and the organic arsenic compound are administered at the same time or within several minutes.

In the present disclosure, the first effective amount of the phenol red is not particularly limited, and can be adjusted according to the severity of the disease. Preferably, the first effective amount is ranged from 0.1 mg to 5.0 mg per kilograms of the subject in need thereof. More preferably, the first effective amount is ranged from 0.5 mg to 1.5 mg per kilograms of the subject in need thereof.

In the present disclosure, the second effective amount of the organic arsenic compound is also not particularly limited, and can be adjusted according to the severity of the disease. Preferably, the second effective amount is ranged from 0.1 mg to 10.0 mg per kilograms of the subject in need thereof. More preferably, the second effective amount is ranged from 0.8 mg to 2.0 mg per kilograms of the subject in need thereof.

In the present disclosure, when the phenol red is formulated into a solution, the first effective amount is ranged from 0.1 mg/cc to 5.0 mg/cc, and preferably from 0.8 mg/cc to 3.0 mg/cc.

In addition, in the present disclosure, when the organic arsenic compound is formulated into a solution, the second effective amount is ranged from 0.1 mg/cc to 10.0 mg/cc, and preferably from 2.0 mg/cc to 6.0 mg/cc.

Other objects, advantages, and novel features of the invention will become more apparent from the following detailed description when taken in conjunction with the accompanying drawings.

BRIEF DESCRIPTION OF THE DRAWINGS

FIG. 1 is a FIGURE showing the leukocyte amount changes of the FIV infected cat during the treatment according to Embodiment 1 of the present disclosure.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

In the following embodiments, a solution containing phenol red (2 mg/cc) and monosodium methanearsonate (4 mg/cc) is used, which is named as "LuMC5", hereinafter. In addition, a solution containing monosodium methanearsonate (4 mg/cc) alone is also used, which is named as "MASA", hereinafter. It should be noted that the following embodiments only provide one formulation of the pharmaceutical composition of the present disclosure. A person skilled in the art knows that the concentration of the active ingredients and the contents of the pharmaceutical composition can be adjusted within the scope of the appended claims.

Embodiment 1

In the present embodiment, feline immunodeficiency virus (FIV) which is belonged to the same family (Retroviridae) and the same genus (*Lentivirus*) to HIV, was selected to perform the present clinical experiment. LuMC5 was administered to the infected cat via intravenous injection or intramuscular injection, 0.4 cc/kg, once or twice a day. The results are shown in the following Table 1 and FIG. 1.

TABLE 1

Blood cells examination data of FIV infected cat during the treatment (Testing company: LEZEN Reference Lab)

|  | WBC | NEU | LYM | MONO | EOSI | BASO |
|---|---|---|---|---|---|---|
| Day 1 | 530 | 18.9 | 43.4 | 37.7 | 0 | 0 |
| Day 3 | 12790 | 73 | 10 | 6.6 | 0.3 | 0.1 |
| Day 9 | 31670 | 80 | 9 | 6 | 4.9 | 0.1 |
| Day 34 | 9000 | 69 | 24 | 5 | 2 | 0.1 |

|  | RBC | Hgb | HCT | M.C.V | M.C.H | M.C.H.C | PLT |
|---|---|---|---|---|---|---|---|
| Day 1 | 7.84 | 12.1 | 44.5 | 56.8 | 15.4 | 27.2 | 56 |
| Day 3 | 7.7 | 11.9 | 42.1 | 54.7 | 15.5 | 28.3 | 165 |
| Day 9 | 6.82 | 10.6 | 34.8 | 51 | 15.5 | 30.5 | 132 |
| Day 34 | 6.71 | 10.2 | 37.5 | 55.9 | 15.2 | 27.2 | 38 |

NEU: Neutrophils/LYM: Lymphocytes/MONO: Monocytes/EOSI: Eosinophils/BASO: Basophils/Hg: Hemoglobin/HCT: Hematocrit/

From the results shown in FIG. 1 and Table 1, the immune cell amount was increased rapidly at Day 3. In addition, acquired immune deficiency syndromes caused by FIV, such as toxoplasmosis, pneumocystis pneumonia and tumors were not found. The FIV infected cat turned into a healthy carrier after treatment.

In addition, LuMC5 can be administered to the FIV infected cat for 4 to 14 days. No virus is detected after 4 to 14 days. Hence, LuMC5 can be administered when the virus levels in the FIV infected cat is high to control the syndromes, and is not have to be administered for a long term. Therefore, the immune system of the FIV infected cat is not destroyed.

Therefore, when LuMC5 is used for treating the FIV infected subject, the development of the acquired immune deficiency syndromes caused by FIV can be inhibited; and the complication such as toxoplasmosis and pneumocystis pneumonia can be inhibited. Hence, the purposes of treatment and prevention can be accomplished.

Embodiment 2

In the present embodiment, MASA and LuMC5 were used to treat the virus infected vertebrate and mammalian. 7 virus species belonged to 5 families were selected to perform the present clinical experiment. Herein, the virus classification is on the basis of National Center for Biotechnology Information, U. S.
Subject: Infected dogs and cates sent to Hei-Ming Veterinary Hospital, Taiwan
7 virus species for clinical experiments:
Family: Retroviridae
   Genus: *Gammaretrovirus*
     species: *Feline leukemia* virus
   Genus: *Lentivirus*
     species: *Feline immunodeficiency* virus
Family: Parvoviridae
   species: *Canine parvovirus*
   species: *Feline panleukopenia* virus
Family: Paramyxoviridae
   Genus: *Morbillivirus*
     species: *Canine distemper* virus
Family: Coronaviridae
   Genus: *Alphacoronavirus*
     species: *Feline coronavirus*
Family: Herpesviridae
   Genus: *Varicellovirus*
     species: *Felid herpesvirus* 1
Treatment: Intravenous injection or intramuscular injection, 0.4 cc/kg, once or twice a day
Testing company: Genomics BioSci & TechCo., Ltd. (Abbreviation: G)
   MountainVet Biotech Co., Ltd. (Abbreviation: M)
   VETE Co., Ltd. (Abbreviation: V)
   LEZEN Reference Lab (Abbreviation: L)
Testing instrument: Real-time quantitative PCR detecting system (sensitivity>99%) for G and M companies; and PCR or RT-PCR for V company
Testing method: The detected genes are the long terminal repeat (LTR) gene of *Feline immunodeficiency* virus, the virus protein 2 (VP2) gene of *Canine parvovirus* and the nucleocapsid gene (N gene) of *Canine distemper* virus. The virus amount is a curve calculated by the cycle threshold ($C_t$) values of the obtained PCR products based on the cycle threshold ($C_t$) values of the standard with predetermined different concentrations.

The testing results of the aforementioned 7 viruses in the clinical experiments are listed in the following Tables 2-1 to 2-7.

TABLE 2-1

Results of the clinical experiments on Feline leukemia virus

| Animal & ID | Age | Gender | Medicine | Total Days | Detecting point | Results (ng/uL) | Specimen | Company |
|---|---|---|---|---|---|---|---|---|
| Cat 130730 | 2 Years | M | MSMA | 9 | Day 0<br>Day 9 | + (*a)<br>− (*b) | Blood | V |

TABLE 2-1-continued

Results of the clinical experiments on Feline leukemia virus

| Animal & ID | Age | Gender | Medicine | Total Days | Detecting point | Results (ng/uL) | Specimen | Company |
|---|---|---|---|---|---|---|---|---|
| Cat 160312 | 7 Years | F | LuMC5 | 9 | Day 0<br>Day 11 | $222.8 \times 10^{-7}$<br>$98.75 \times 10^{-7}$ | Blood | M |
| Cat 150903 | 1 Years | F | LuMC5 | 7 | Day 0<br>Day 9 | $248.8 \times 10^{-7}$<br>$87.51 \times 10^{-7}$ | Blood | M |
| Cat 160729 | 2 Months | F | LuMC5 | 6 | Day 0<br>Day 4<br>Day 6 | $261.4 \times 10^{-7}$<br>$74.6 \times 10^{-7}$<br>$53.6 \times 10^{-7}$ | Blood | M |

TABLE 2-2

Results of the clinical experiments on feline immunodeficiency virus

| Animal & ID | Age | Gender | Medicine | Total Days | Detecting point | Results (ng/uL) | Specimen | Company |
|---|---|---|---|---|---|---|---|---|
| Cat 130730 | 2 Years | M | MSMA | 9 | Day 0<br>Day 9 | + (*a)<br>− (*b) | Blood | V |
| Cat 130805 | 7 Months | F | MSMA | 14 | Day 0<br>Day 14 | + (*a)<br>− (*b) | Blood | V |
| Cat 160312 | 7 Years | F | LuMC5 | 9 | Day 0<br>Day 11 | $45.75 \times 10^{-7}$<br>• | Blood | M |
| Cat 160729 | 2 Months | F | LuMC5 | 6 | Day 0<br>Day 4<br>Day 6 | $34.8 \times 10^{-7}$<br>•<br>• | Blood | M |

TABLE 2-3

Results of the clinical experiments on canine parvovirus

| Animal & ID | Age | Gender | Medicine | Total Days | Detecting point | Results (ng/uL) | Specimen | Company |
|---|---|---|---|---|---|---|---|---|
| Dog 140529 | 6 Months | F | MSMA | 4 | Day 0<br>Day 4 | $932918 \times 10^{-8}$<br>$28836 \times 10^{-8}$ | Feces (*c) | G |
| Dog 150716 | 3 Months | F | MSMA | 10 | Day 0<br>Day 10 | $458306 \times 10^{-8}$<br>$2470 \times 10^{-8}$ | Blood<br>Feces (*d) | M |
| Dog 150708 | 2 Months | F | MSMA | 10 | Day 0<br>Day 8<br>Day 15 | $40724.24 \times 10^{-7}$<br>$2696.9 \times 10^{-7}$<br>$185.6 \times 10^{-7}$ | Blood | M |
| Dog 150125 | 1 year | M | MSMA | 7 | Day 0<br>Day 3<br>Day 5<br>Day 6<br>Day 11 | $46322 \times 10^{-8}$<br>$345 \times 10^{-8}$<br>$75 \times 10^{-8}$<br>$40 \times 10^{-8}$<br>• | Blood | G |
| Dog 140413 | 5 Months | F | MSMA | 10 | Day 0<br>Day 3<br>Day 9<br>Day 11 | $105804 \times 10^{-8}$<br>$3560 \times 10^{-8}$<br>$5314 \times 10^{-8}$<br>$183.7 \times 10^{-8}$ | Blood | G |
| Dog 151123 | 2 Months | M | LuMC5 | 3 | Day 0<br>Day 3 | $36630.6 \times 10^{-7}$<br>$1111.5 \times 10^{-7}$ | Blood | M |
| Dog 160301 | 3 Months | M | LuMC5 | 5 | Day 0<br>Day 5 | $102094.9 \times 10^{-7}$<br>$66.9 \times 10^{-7}$ | Blood | M |
| Dog 160308 | 5 Months | M | LuMC5 | 4 | Day 0<br>Day 4 | $62749.9 \times 10^{-7}$<br>$7.61 \times 10^{-7}$ | Blood | M |
| Dog 160311 | 3 Months | M | LuMC5 | 4 | Day 0<br>Day 4 | $6.66 \times 10^{-7}$<br>• | Blood | M |
| Dog 160324 | 5 Years | M | LuMC5 | 3 | Day 0<br>Day 3 | $6474.4 \times 10^{-7}$<br>$87.7 \times 10^{-7}$ | Blood | M |
| Dog 160326 | 8 Months | F | LuMC5 | 4 | Day 0<br>Day 3 | $107633.3 \times 10^{-7}$<br>$77.4 \times 10^{-7}$ | Blood | M |

TABLE 2-4

Results of the clinical experiments on feline panleukopenia virus

| Animal & ID | Age | Gender | Medicine | Total Days | Detecting point | Results (ng/uL) | Specimen | Company |
|---|---|---|---|---|---|---|---|---|
| Cat 150323 | 3 Months | F | MSMA | 12 | Day 0<br>Day 6<br>Day 15<br>Day 21 | $4240717 \times 10^{-8}$<br>$22391915 \times 10^{-8}$<br>$711 \times 10^{-8}$<br>$14 \times 10^{-8}$ | Feces (*c_) | G |
| Cat 141128 | 3 Months | M | MSMA | 10 | Day 0<br>Day 6<br>Day 7<br>Day 8 | $130942 \times 10^{-8}$<br>$1088 \times 10^{-8}$<br>$25 \times 10^{-8}$<br>$79 \times 10^{-8}$ | Blood | G |
| Cat 140512 | 3 Years | F | MSMA | 8 | Day 0<br>Day 7 | $143.67 \times 10^{-7}$<br>• | Blood | G |
| Cat 150529 | 3 Years | F | MSMA | 12 | Day 0<br>Day 15 | $121.7 \times 10^{-7}$<br>• | Blood | G |
| Cat 150826 | 7 Months | M | LuMC5 | 7 | Day 0<br>Day 5 | $11.21 \times 10^{-7}$<br>$2.47 \times 10^{-7}$ | Feces (*c) | M |
| Cat 160104 | 8 Months | M | LuMC5 | 8 | Day 0<br>Day 8 | $40784.1 \times 10^{-7}$<br>$10.28 \times 10^{-7}$ | Blood | M |
| Cat 160108 | 8 Months | F | LuMC5 | 7 | Day 0<br>Day 7 | $4219.6 \times 10^{-7}$<br>$78.91 \times 10^{-7}$ | Blood | M |

TABLE 2-5

Results of the clinical experiments on canine distemper virus

| Animal & ID | Age | Gender | Medicine | Total Days | Detecting point | Results (ng/uL) | Specimen | Company |
|---|---|---|---|---|---|---|---|---|
| Dog 140701 | 4 Months | F | MSMA | 14 | Day 0<br>Day 4<br>Day 10<br>Day 14 | $1341 \times 10^{-8}$<br>$334 \times 10^{-8}$<br>$116 \times 10^{-8}$<br>• | Nasal secretion (*c) | G |
| Dog 140703 | 4 Months | F | MSMA | 12 | Day 0<br>Day 3<br>Day 10<br>Day 12 | $24 \times 10^{-8}$<br>$312 \times 10^{-8}$<br>$61 \times 10^{-8}$<br>• | Nasal secretion (*c) | G |
| Dog 140808 | 1 Year | F | MSMA | 11 | Day 0<br>Day 7<br>Day 11 | $310 \times 10^{-8}$<br>$350 \times 10^{-8}$<br>• | Blood | G |
| Dog 140808-1 | 7 Years | F | MSMA | 12 | Day 0<br>Day 8<br>Day 12 | $350 \times 10^{-8}$<br>$264 \times 10^{-8}$<br>• | Blood | G |
| Dog 140617 | 12 Years | M | MSMA | 3 | Day 0<br>Day 3 | $28 \times 10^{-8}$<br>• | Blood | G |

TABLE 2-6

Results of the clinical experiments on feline coronavirus

| Animal & ID | Age | Gender | Medicine | Total Days | Detecting point | Results (ng/uL) | Specimen | Company |
|---|---|---|---|---|---|---|---|---|
| Cat 150430 | 5 Years | F | MSMA | 8 | Day 0<br>Day 8 | $41733.8 \times 10^{-7}$<br>• | Blood | G |
| Cat 150826 | 4 Months | M | LuMC5 | 8 | Day 0<br>Day 5<br>Day 8 | $5691.51 \times 10^{-7}$<br>$176.05 \times 10^{-7}$<br>• | Feces (*c) | M |
| Cat 150903 | 5 Months | M | LuMC5 | 5 | Day 0<br>Day 5 | $10589.77 \times 10^{-7}$<br>• | Blood | M |
| Cat 160110 | 7 Months | F | LuMC5 | 8 | Day 0<br>Day 8 | $125.8 \times 10^{-7}$<br>• | Blood<br>Ascites | M |

TABLE 2-7

Results of the clinical experiments on felid herpesvirus 1

| Animal & ID | Age | Gender | Medicine | Total Days | Detecting point | Results (ng/uL) | Specimen | Company |
|---|---|---|---|---|---|---|---|---|
| Cat 150417 | 1 Year | M | MSMA | 12 | Day 0<br>Day 4<br>Day 13 | $1528214 \times 10^{-8}$<br>$214 \times 10^{-8}$<br>• | Blood | G |
| Cat 150502 | 5 Months | M | MSMA | 10 | Day 0<br>Day 10 | $151.8 \times 10^{-7}$<br>$3.75 \times 10^{-7}$ | Nasal secretion (*c) | G |
| Cat 150507 | 3 years | F | MSMA | 9 | Day 0<br>Day 7 | $27380 \times 10^{-7}$<br>• | Blood | G |
| Cat 150516 | 8 Months | F | MSMA | 8 | Day 0<br>Day 15 | $2282.5 \times 10^{-7}$<br>$69.71 \times 10^{-7}$ | Blood | G |
| Cat 151224 | 8 Months | F | LuMC5 | 5 | Day 0<br>Day 5 | $326.1 \times 10^{-7}$<br>• | Blood | M |
| Cat 160315 | 11 Months | F | LuMC5 | 6 | Day 0<br>Day 6 | $8911.7 \times 10^{-7}$<br>$661.6 \times 10^{-7}$ | Blood | M |

(*a) "+" refers to viruses were found in the detection.
(*b) "−" refers to viruses were not found in the detection.
(*c) Not quantitative detection
• No pathogen infection or small amount of pathogens detected The administered period of MASA was 4 days to 14 days (average 9 days). The administered period of LuMC5 was 3 days to 9 days (average 5.7 days). When LuMC5 was administered via subcutaneous injection, intramuscular injection or intravenous injection, the fever in the subject was reduced within 3 hours to 5 hours, and metal condition of the subject was improved. The virus level in the specimens thereof was greatly reduced to slight amount within 2 days to 5 days, and reduced from the slight amount to the amount incapable to be detected within 5 days to 8 days. The infection syndromes were rapidly improved.

Embodiment 3

In the present embodiment, LuMC5 was used to treat the mammalian with hemorrhagic venom infection and neurotoxic venom.

Subject: Infected dogs and cates sent to Hei-Ming Veterinary Hospital, Taiwan

Treatment: Intravenous injection or intramuscular injection, 0.4 cc/kg, once or twice a day The testing results s in the clinical experiments of the present embodiment are listed in the following Tables 3-1 to 3-3.

TABLE 3-1

Results of the clinical experiments on the subject infected with hemorrhagic venom infection of *Trimeresurus mucrosquamatus*

| Animal & ID | Age | Gender | Time to be treated | Administered times | Syndromes before treatment<br>Condition after treatment |
|---|---|---|---|---|---|
| Dog 130420 | 3 years | M | 2 hours after infection | 1 | Depression, lifeless, sticky saliva, and facial and head swelling<br>Depression and lifeless were relieved, 1 hours after treatment.<br>Facial and head swelling were relieved, 12 hours after treatment. |
| Dog 140405 | 6 years | F | 2 hours after infection | 2 | Facial swelling, depression, lifeless, and mouth and tongue blood stasis<br>Depression and lifeless were relieved, 30 minutes after treatment.<br>Facial swelling and mouth and tongue blood stasis were relieved, 24 hours after treatment. |
| Cat 140320 | 1 year | F | 1 hours after infection | 2 | Shock, unconsciousness, tachypnoea, transparent and jelly-like saliva, and hematuria<br>Shock, unconsciousness, tachypnoea, and transparent and jelly-like saliva were relieved, 30 minutes after treatment.<br>Hematuria was relieved and the subject became healthy, 50 minutes after treatment. |
| Dog 140724 | 3 years | M | 26 hours after infection | 2 | Depression, lifeless, sticky saliva, and chin swelling<br>Depression, lifeless, and sticky saliva were relieved, 50 minutes after treatment.<br>Chin swelling was relieved, 12 hours after treatment. |
| Dog 140707 | 4 years | M | 4 hours after | 1 | Bleed and depression<br>Bleed caused by snakebite was relieved, 10 |

TABLE 3-1-continued

Results of the clinical experiments on the subject infected with hemorrhagic venom infection of *Trimeresurus mucrosquamatus*

| Animal & ID | Age | Gender | Time to be treated | Administered times | Syndromes before treatment / Condition after treatment |
|---|---|---|---|---|---|
| | | | infection | | minutes after treatment. Depression was relieved, 30 minutes after treatment. |
| Dog 140707-1 | 4 years | M | 4 hours after infection | 1 | Bleed and depression. Bleed caused by snakebite was relieved, 10 minutes after treatment. Depression was relieved, 30 minutes after treatment. |
| Dog 141028 | 7 years | M | 16 hours after infection | 2 | Depression, lifeless, sticky saliva, and facial and chin swelling. Depression and lifeless were relieved, 30 minutes after treatment. Facial and chin swelling was relieved, 12 hours after treatment. |

TABLE 3-2

Results of the clinical experiments on the subject infected with hemorrhagic venom infection of *Viridovipera stejnegeri*

| Animal & ID | Age | Gender | Time to be treated | Administered times | Syndromes before treatment / Condition after treatment |
|---|---|---|---|---|---|
| Dog 140412 | 1 year | M | 14 hours after infection | 3 | Depression, lifeless, sticky saliva, and facial and chin swelling. Depression and lifeless were relieved, 2 hours after treatment. Facial and chin swelling was relieved, 24 hours after treatment. |

TABLE 3-3

Results of the clinical experiments on the subject infected with neurotoxic venom infection of *Naja*

| Animal & ID | Age | Gender | Time to be treated | Administered times | Syndromes before treatment / Condition after treatment |
|---|---|---|---|---|---|
| Dog 140426 | 6 years | M | 2 hours after infection | 2 | Depression, lifeless, sticky saliva, and facial and chin swelling. Depression and lifeless were relieved, 30 minutes after treatment. Facial and chin swelling was relieved, 12 hours after treatment. |

From the results shown in the present embodiment, when LuMC5 was administered into the infected subject via subcutaneous injection, intramuscular injection or intravenous injection, the nose bleeding and sticky saliva can be relieved within 10 minutes, the depression can be relieved within 30 minutes, the hematuria can be relieved within 50 minutes, and the swelling can be relieved and the treated subject become healthy within 1 hours to 36 hours. Hence, by using LuMC5 of the present disclosure, the infection syndromes can be controlled. Compared to the conventional method by naturalizing toxins with serum formulation, in which antibodies are formed to identify and neutralize toxin proteins after 7 days to 14 days and the swelling syndrome is relieved after 7 days, LuMC5 of the present disclosure can relieve the syndromes in a short time and has superior treatment efficacy.

Embodiment 4

In the present embodiment, LuMC5 was used to treat the mammalian that the mosquito, bee, scorpion, spider, centipede, ant, and staphylinidae bitten.

Subject: Dog bit by bees, sent to Hei-Ming Veterinary Hospital, Taiwan, and having bodyweight of 27 Kg Treatment: Intravenous injection or intramuscular injection, 0.4 cc/kg, twice a day The result is shown in the following Table 4-1.

TABLE 4-1

| Animal & ID | Age | Gender | Time to be treated | Administered times | Syndromes before treatment / Condition after treatment |
|---|---|---|---|---|---|
| Dog 140414 | 14 years | F | 2 hours after infection | 2 | Depression, lifeless, and facial and head swelling. Depression and lifeless were relieved, 30 minutes after treatment. Facial and head swelling was relieved, 12 hours after treatment. |

The treatment results show that the mental condition of the treated subject was improved, the appetite thereof was recovered, and the activity thereof such as tail shaking turned into normal, after treatment.

Subject: Human bit by a mosquito, bodyweight: 79 Kg

Treatment: Applying LuMC5 at the mosquito biting region, twice a day

The result is shown in the following Table 4-2.

TABLE 4-2

| Animal & ID | Age | Gender | Time to be treated | Administered times | Syndromes before treatment Condition after treatment |
|---|---|---|---|---|---|
| Dog 160415 | 55 years | F | 3 minutes after infection | 2 | Swelling and itch at the biting region on the skin Itch was relieved, 3-20 minutes after applying medicine. Swelling was relieved, 1-3 hours after applying medicine. |

From the results shown in the present embodiment, LuMC5 can effectively relieve the itch and selling on the skin caused by the insects. If the subject is bit by the insects, the glycosylation of the virus can be inhibited when LuMC5 is applied immediately. In addition, the syndromes of venom allergy, fever and lifeless can be relieved by administering LuMC5 via injection. The swelling at the skin region bit by the insects with pathogens can be relieved by applying ointment or solution at the affected region. Therefore, Dengue virus, West Nile virus and Zika virus infection to human and animals can be effectively relieved and prevented by using LuMC5 of the present disclosure.

Embodiment 5

In the present embodiment, LuMC5 was used to treat cataract and retinopathy caused by abnormal eye cells in mammalian.

Subject: Infected dogs and cates sent to Hei-Ming Veterinary Hospital, Taiwan

Treatment: Solution containing 1-2 mg/cc of phenol red and 3-4 mg/cc of monosodium methanearsonate, one drop per time, twice or three times a day The result is shown in the following Tables 5-1 and 5-2.

TABLE 5-1

Results of the clinical experiments on Pomeranian with cataract

| Animal & ID | Age | Gender | Total days | Treatment | Syndromes before treatment Condition after treatment |
|---|---|---|---|---|---|
| Dog 151013 | 18 years | F | 46 | One drop per time, three times a day | Mature cataract, spin around while walking, incapable of walking straight, hitting the wall, and recognizing surrounding by smelling, auditory sense and living experience The clouding of the lens in the eye reduced. The treated subject can walk straight without hitting the wall. |

TABLE 5-2

Results of the clinical experiments on Golden Retriever with cataract

| Animal & ID | Age | Gender | Total days | Treatment | Syndromes before treatment Condition after treatment |
|---|---|---|---|---|---|
| Dog 160128 | 10 years | M | 29 | One drop per time, twice a day | The subject cannot see the object at the long distance during daytime. Visually impaired during the night. The clouding of the lens in the eye reduced. The subject's day and night vision was recovered. |

Embodiment 6

In the present embodiment, LuMC5 was used to treat metabolism-related diseases (including pancreatitis, kidney inflammation, hepatitis, and cholangitis) occurred in mammalian.

Subject: Infected dogs and cates sent to Hei-Ming Veterinary Hospital, Taiwan

Treatment: Intravenous injection or intramuscular injection, 0.4 cc/kg, once a day Testing company: LEZEN Reference Lab The result is shown in the following Tables 6-1 to 6-4.

TABLE 6-1

| Animal & ID | Age | Gender | Total days | Body weight | Syndromes before treatment Condition after treatment |
|---|---|---|---|---|---|
| Dog 160714 | 15 years | M | 11 | 20 Kg | Anorexia for 4-5 days, urine in dark brown, weakness, and dehydration Appetite and activity recovered |

TABLE 6-2

Blood test data of Dog 160714 during the treatment

| | PT:ALT (liver) | Alkaline-p (gall) | BUN (uremia) | Creatinine (Kidney) | Amylase (pancreas) |
|---|---|---|---|---|---|
| Day 1 | 87 | 87 | 94.2 | 3.44 | 1447 |
| Day 19 | 24 | 50 | 60 | 2.78 | 1225 |
| Reference | 14-40 U/L | 32-91 U/L | 8-20 mg/dL | 0.64-1.27 mg/dL | S: 28-1200 U/L |

TABLE 6-3

| Animal & ID | Age | Gender | Total days | Body weight | Syndromes before treatment Condition after treatment |
|---|---|---|---|---|---|
| Dog 160805 | 15 years | F | 3 | 28 Kg | Anorexia for 1-2 days, vomit, weakness, incapable of standing Capable of standing at Day 2, eating small amount of food, and walking slowly at Day 3 |

TABLE 6-4

Blood test data of Dog 160805 during the treatment

| Item | BUN (uremia) | Creatinine (Kidney) | Amylase (pancreas) |
|---|---|---|---|
| 2016 Aug. 5 | 31.5 | 2.46 | 1251 |
| 2016 Aug. 8 | 21.5 | 1.19 | 931 |
| Reference | 8-20 mg/dL | 0.64-1.27 mg/dL | S: 28-1200 U/L |

From the results shown in Embodiments 5 and 6, a solution made from LuMC5 can be used to treat diseases caused by abnormal eye cells (such as cataract and retinopathy) by administering the solution at the predetermined time with a predetermined amount. When treating diseases caused by abnormal brain cells (including Alzheimer's Disease and Parkinson's disease), LuMC5 can be formulated into a paste or ointment and administered at the predetermined time with a predetermined amount. The skin absorbs the active ingredients, and the active ingredients can enter into the brain via the blood in the carotid artery to accomplish the purpose of preventing disease. When treating metabolism related diseases (such as pancreatitis, kidney inflammation, hepatitis, as cholangitis), LuMC5 can be administered via subcutaneous injection, intramuscular injection or intravenous injection for 5 to 7 days, and the swelling and inflammation can be effectively relieved.

Embodiment 7

When treating prion infection (including bovine spongiform encephalopathy, scrapie, and creutzfeldt-Jakob disease), LuMC5 can be formulated into a paste or ointment and administered at the predetermined time with a predetermined amount. The skin absorbs the active ingredients, and the active ingredients can enter into the brain via the blood in the carotid artery to accomplish the purpose of preventing disease.

Although the present invention has been explained in relation to its preferred embodiment, it is to be understood that many other possible modifications and variations can be made without departing from the spirit and scope of the invention as hereinafter claimed.

What is claimed is:

1. A method for treating a glycoprotein-related disease, comprising:
   administering a first effective amount of phenol red and a second effective amount of an organic arsenic compound to a mammal in need thereof;
   wherein the glycoprotein-related disease is caused by one virus selected from the group consisting of: feline leukemia virus, feline immunodeficiency virus, canine parvovirus, feline panleukopenia virus, feline coronavirus and feline herpesvirus 1; and
   wherein the organic arsenic compound is monosodium methanearsonate.

2. The method of claim 1, wherein a pharmaceutical acceptable carrier is further administered to the mammal in need thereof.

3. The method of claim 2, wherein the pharmaceutical acceptable carrier is selected from the group consisting of solvent, buffer, suspending agent, decomposer, disintegrating agent, dispersing agent, binding agent, excipient, stabilizing agent, chelating agent, diluent, gelling agent, preservative, lubricant, absorption delaying agent, and liposome.

4. The method of claim 1, wherein the first effective amount is ranged from 0.1 mg to 5.0 mg per kilograms of the mammal in need thereof.

5. The method of claim 4, wherein the first effective amount is ranged from 0.5 mg to 1.5 mg per kilograms of the mammal in need thereof.

6. The method of claim 1, wherein the first effective amount is ranged from 0.1 mg/cc to 5.0 mg/cc.

7. The method of claim 1, wherein the first effective amount is ranged from 0.8 mg/cc to 3.0 mg/cc.

8. The method of claim 1, wherein the second effective amount is ranged from 0.1 mg to 10.0 mg per kilograms of the mammal in need thereof.

9. The method of claim 8, wherein the second effective amount is ranged from 0.8 mg to 2.0 mg per kilograms of the mammal in need thereof.

10. The method of claim 1, wherein the second effective amount is ranged from 0.1 mg/cc to 10.0 mg/cc.

11. The method of claim 10, wherein the second effective amount is ranged from 2.0 mg/cc to 6.0 mg/cc.

* * * * *